(12) United States Patent
Robichaud

(10) Patent No.: US 12,171,473 B2
(45) Date of Patent: Dec. 24, 2024

(54) OSTEOTOMY PLATE AND METHOD FOR PERFORMING AN OSTEOTOMY PROCEDURE USING THE SAME

(71) Applicant: LABORATOIRES BODYCAD INC., Québec (CA)

(72) Inventor: Jean Robichaud, St- Aubert (CA)

(73) Assignee: LABORATOIRES BODYCAD INC., Québec (CA)

(*) Notice: Subject to any disclaimer, the term of this patent is extended or adjusted under 35 U.S.C. 154(b) by 502 days.

(21) Appl. No.: 17/306,364

(22) Filed: May 3, 2021

(65) Prior Publication Data

US 2021/0338291 A1   Nov. 4, 2021

Related U.S. Application Data

(60) Provisional application No. 63/019,595, filed on May 4, 2020.

(51) Int. Cl.
*A61B 17/80* (2006.01)
*A61B 17/17* (2006.01)
(Continued)

(52) U.S. Cl.
CPC ........ *A61B 17/746* (2013.01); *A61B 17/1721* (2013.01); *A61B 17/8095* (2013.01); *A61B 2017/565* (2013.01); *A61B 2017/568* (2013.01)

(58) Field of Classification Search
CPC ............ A61B 17/152; A61B 2017/568; A61B 2017/565; A61B 17/746; A61B 17/8095
See application file for complete search history.

(56) References Cited

U.S. PATENT DOCUMENTS

| 4,263,904 A | * | 4/1981 | Judet | A61B 17/68 |
| | | | | 606/281 |
| 5,053,039 A | * | 10/1991 | Hofmann | A61B 17/15 |
| | | | | 606/86 R |

(Continued)

FOREIGN PATENT DOCUMENTS

| CN | 102420519 A | 4/2012 |
| WO | WO-2013/101979 A1 | 7/2013 |

(Continued)

OTHER PUBLICATIONS

Search Report under Section 17 issued by the United Kingdom Intellectual Property Office for GB Application No. 2106201.3, dated Aug. 11, 2021.

*Primary Examiner* — David W Bates
(74) *Attorney, Agent, or Firm* — MARSHALL, GERSTEIN & BORUN LLP

(57) ABSTRACT

A fixation plate for securing together adjacent first and second bone sections of a bone with a bone cut extending thereinbetween, the fixation plate comprising: a first fixation portion having a bone interface side superposable against the first bone section and a second fixation portion extending away from the first fixation portion, the second fixation portion including a holding portion shaped to conform to an outer surface of the second bone section when superposed thereto and when the first and second bone sections are at a predetermined angular orientation relative to each other such that a snug fit of the second bone section with the holding portion provides an indication that the first and second bone sections are at the predetermined angular orientation relative to each other.

19 Claims, 10 Drawing Sheets

(51) Int. Cl.
*A61B 17/56* (2006.01)
*A61B 17/74* (2006.01)

(56) References Cited

U.S. PATENT DOCUMENTS

| | | | | |
|---|---|---|---|---|
| 5,916,220 A | * | 6/1999 | Masini | A61B 17/155 606/88 |
| 6,007,538 A | * | 12/1999 | Levin | A61B 17/8076 606/907 |
| 7,635,365 B2 | * | 12/2009 | Ellis | A61B 17/8076 606/71 |
| 9,414,846 B2 | * | 8/2016 | Gillman | A61B 17/155 |
| 9,775,657 B2 | * | 10/2017 | Bernstein | A61B 17/80 |
| 9,788,872 B2 | * | 10/2017 | Wagner | A61B 17/80 |
| 10,456,273 B2 | * | 10/2019 | Robichaud | A61F 2/4657 |
| 11,571,312 B1 | * | 2/2023 | Parekh | A61B 17/1728 |
| 2004/0153086 A1 | * | 8/2004 | Sanford | A61F 2/4684 606/88 |
| 2007/0226986 A1 | * | 10/2007 | Park | A61B 17/1675 29/592 |
| 2009/0210010 A1 | * | 8/2009 | Strnad | A61B 17/8061 606/280 |
| 2009/0312758 A1 | * | 12/2009 | Petit | A61B 17/809 606/60 |
| 2010/0106197 A1 | * | 4/2010 | Buscher | A61B 17/151 606/286 |
| 2010/0152782 A1 | | 6/2010 | Stone et al. | |
| 2011/0106093 A1 | * | 5/2011 | Romano | A61B 17/1675 606/88 |
| 2011/0144760 A1 | * | 6/2011 | Wong | A61F 2/4657 623/20.14 |
| 2011/0213376 A1 | | 9/2011 | Maxson et al. | |
| 2012/0010710 A1 | * | 1/2012 | Frigg | A61B 34/10 623/16.11 |
| 2012/0029574 A1 | * | 2/2012 | Furrer | A61B 17/151 606/280 |
| 2012/0041445 A1 | * | 2/2012 | Roose | A61B 17/1746 606/96 |
| 2012/0116562 A1 | * | 5/2012 | Agnihotri | A61B 34/10 700/98 |
| 2012/0271366 A1 | * | 10/2012 | Katrana | A61B 17/8866 606/86 R |
| 2012/0296339 A1 | * | 11/2012 | Iannotti | A61B 17/1703 606/86 R |
| 2013/0090695 A1 | * | 4/2013 | Bernstein | A61B 17/808 606/281 |
| 2014/0066937 A1 | * | 3/2014 | Wiebe, III | A61B 17/8897 606/88 |
| 2014/0074100 A1 | * | 3/2014 | Murray | A61B 17/1764 606/88 |
| 2014/0074438 A1 | * | 3/2014 | Furrer | A61B 17/8071 703/1 |
| 2014/0180343 A1 | * | 6/2014 | Gaudin | A61F 2/4225 606/283 |
| 2015/0051650 A1 | * | 2/2015 | Verstreken | G16Z 99/00 606/281 |
| 2015/0209093 A1 | * | 7/2015 | Dallis | A61B 17/8061 606/281 |
| 2015/0305752 A1 | | 10/2015 | Eash | |
| 2016/0367300 A1 | * | 12/2016 | Caldarella | A61B 17/82 |
| 2017/0360453 A1 | * | 12/2017 | Brailovski | A61B 17/1728 |
| 2018/0116804 A1 | * | 5/2018 | Hafez | A61F 2/38 |
| 2018/0263700 A1 | * | 9/2018 | Gillman | A61B 17/1778 |
| 2018/0317986 A1 | * | 11/2018 | Jackman | A61B 17/151 |
| 2019/0159819 A1 | * | 5/2019 | Fatone | A61B 17/8019 |
| 2020/0352582 A1 | * | 11/2020 | Larche | A61B 17/1764 |
| 2021/0022879 A1 | * | 1/2021 | Hollis | A61F 2/4225 |
| 2021/0077192 A1 | * | 3/2021 | Perler | A61B 17/1775 |
| 2021/0100596 A1 | * | 4/2021 | Simpson | A61B 17/88 |
| 2022/0061899 A1 | * | 3/2022 | Destainville | B33Y 50/00 |
| 2022/0110641 A1 | * | 4/2022 | Zink | A61B 17/1635 |

FOREIGN PATENT DOCUMENTS

| | | |
|---|---|---|
| WO | WO-2019/038240 A1 | 2/2019 |
| WO | WO-2020/037420 A1 | 2/2020 |
| WO | WO-2020/037421 A1 | 2/2020 |

* cited by examiner

OSTEOTOMY PLATE AND METHOD FOR PERFORMING AN OSTEOTOMY PROCEDURE USING THE SAME

CROSS-REFERENCE TO RELATED APPLICATION(S)

The present application claims the benefit of U.S. Provisional Application No. 63/019,595 filed on May 4, 2020, the specification of which is incorporated herein by reference.

TECHNICAL FIELD

The technical field generally relates to osteotomy fixation plates, and more specifically to osteotomy fixation plates for use in an osteotomy procedure, to methods for performing an osteotomy and to kits for use in a femoral osteotomy procedure.

BACKGROUND

Osteotomy procedures involve cutting a patient's bone in order to shorten or lengthen it or to modify its alignment. The procedure can be one of an open-wedge osteotomy or a closing wedge osteotomy. In a closing-wedge osteotomy procedure, a wedge-shaped piece of bone is removed from the bone, such as a femur, a tibia, a humerus, a radius/ulna (forearm) and multiple foot bones, to form a wedge opening in the bone. The wedge opening thereby divides the bone into upper (or proximal) and lower (or distal) bone sections. The bone is then mechanically closed to bring the proximal and distal bone sections in abutment with each other. Specifically, the wedge opening does not extend through the entire cross-section of the bone such that the proximal and distal bone sections are still attached together by a thin piece of bone which acts as a hinge when the proximal and distal bone sections are pivoted towards each other. The proximal and distal bone sections are then maintained together using an osteotomy plate or fixation plate which overlaps the proximal and distal bone sections and is fastened to the bone.

Unfortunately, during the closure of the bone, it is possible for the thin piece of bone to twist, or even break. In this case, the proximal bone section may rotate relative to the distal bone section about a bone axis extending longitudinally. It may therefore become difficult for the person performing the surgery to realign the proximal and distal bone sections in their initial angular alignment. Moreover, current fixation plates and osteotomy techniques do not provide any solution to readily realign the bone sections relative to each other.

SUMMARY

According to one aspect, there is provided a fixation plate for securing together adjacent first and second bone sections of a bone with a bone cut extending thereinbetween, the fixation plate comprising: a first fixation portion having a bone interface side superposable against the first bone section and securable to the first bone section; a second fixation portion extending away from the first fixation portion, the second fixation portion having a bone interface side superposable against the second bone section and being securable to the second bone section, the second fixation portion including a holding portion, the bone interface side of the holding portion being shaped to conform to an outer surface of the second bone section when superposed thereto and when the first and second bone sections are at a predetermined angular orientation relative to each other such that a snug fit of the second bone section with the holding portion provides an indication that the first and second bone sections are at the predetermined angular orientation relative to each other.

In at least one embodiment, the bone extends along a bone axis and the second fixation portion includes an elongated central portion extending substantially parallel to the bone axis when the fixation plate is secured to the first and second bone sections, and wherein the holding portion comprises at least one holding arm extending laterally from the elongated central portion to partially surround the second bone section.

In at least one embodiment, the at least one holding arm includes first and second holding arms extending from either side of the elongated central portion.

In at least one embodiment, the first and second holding arms are in alignment with each other along the elongated central portion.

In at least one embodiment, the first and second holding arms are offset from each other along the elongated central portion.

In at least one embodiment, the second fixation portion is substantially cross-shaped and each one of the first and second holding arms includes a free arm end located away from the elongated central portion, the free arm end of the first holding arm being spaced from the free arm end of the second holding arm.

In at least one embodiment, the first and second holding arms are sized and shaped such that when the first fixation portion is superposed against the first bone portion and the second fixation portion is superposed against the second fixation portion, the first holding arm defines a first arm axis extending between the free arm end of the first holding arm and a substantial center of the bone and the second holding arm defines a second arm axis extending between the free arm end of the second holding arm and the substantial center of the bone, the first and second arm axes are angled away from each other at an arm spacing angle ranging between about 15 degrees and about 180 degrees.

In at least one embodiment, the arm spacing angle is between about 20 degrees and about 150 degrees.

In at least one embodiment, the arm spacing angle is between about 30 degrees and about 110 degrees.

In at least one embodiment, the arm spacing angle is between about 40 degrees and about 100 degrees.

In at least one embodiment, the arm spacing angle is less than about 110 degrees.

In at least one embodiment, the bone cut defines a cutting plane interface along which the first and the second bone sections meet.

In at least one embodiment, the first fixation portion is a distal fixation portion and the second fixation portion is a proximal fixation portion.

In at least one embodiment, the fixation plate includes a plurality of fastener holes sized and shaped for receiving fasteners to secure the fixation plate to the bone, the plurality of fastener holes including at least one distal portion fastener hole defined in the distal fixation portion and at least one proximal portion fastener hole defined in the proximal fixation portion.

In at least one embodiment, the at least one distal portion fastener hole includes at least three distal portion fastener holes.

In at least one embodiment, the at least one proximal portion fastener hole includes first and second proximal portion fastener holes defined in the first and second holding arms.

In at least one embodiment, the at least one proximal portion fastener hole includes at least one central portion fastener hole defined in the elongated central portion of the proximal fixation portion.

In at least one embodiment, the fixation plate further comprises an outward facing side located opposite the bone interface side of the first and second fixation portions, the fixation plate further comprising a plurality of grommet projections extending away from of the outward facing side, each grommet projection surrounding a corresponding one of the fastener holes.

In at least one embodiment, each one of the grommet projections is sized and shaped to receive a fastener head of a fastener when the fastener extends through the corresponding one of the fastener holes such that the fastener head is at least partially sunk in a corresponding one of the grommet projections.

In at least one embodiment, the grommet projections are filleted inwardly.

In at least one embodiment, the bone interface side of the second fixation portion is patient-specific.

According to another aspect, there is also provided a method for performing an osteotomy procedure, the method comprising: cutting a patient's bone to form a bone cut in the bone, the bone cut dividing the patient's bone into distal and proximal bone sections located on either side of the bone cut; angularly aligning the distal and proximal bone sections relative to each other at a predetermined angular orientation relative to each other; positioning a fixation plate against the patient's bone such that a distal fixation portion of the fixation plate overlaps the distal bone section and a proximal fixation portion of the fixation plate overlaps the proximal bone section with the proximal bone section snuggly fitting against a holding portion of at least one of the distal and proximal fixation portions, the holding portion having a bone interface side being shaped to conform to a curved outer surface of the patient's bone when superposed thereto with the distal and proximal bone sections being configured at the predetermined angular orientation relative to each other; and securing together the distal and proximal bone sections by inserting fasteners into fastening holes defined in the fixation plate.

In at least one embodiment, cutting the patient's bone comprises: cutting out a bone wedge portion from the patient's bone by performing two substantially planar cuts extending substantially along two cutting planes intersecting each other at an angle; removing the cut bone wedge portion from the patient's bone to define the wedge opening; and pivoting the distal and proximal bone sections towards each other until the distal and proximal bone sections abut each other to close the wedge opening and to thereby define the bone cut between the distal and proximal bone.

In at least one embodiment, performing the two substantially planar cuts includes: positioning a patient-specific surgical cutting guide against the patient's bone; inserting a cutting tool into the patient's bone through a first wedge cutting slot defined in the cutting guide; inserting the cutting tool through a second wedge cutting slot defined in the cutting guide.

In at least one embodiment, the fixation plate comprises fastener holes extending therethrough with at least one of the fastener holes being located in the proximal bone section and at least one of the fastener holes being located in the distal bone section, the method further comprising: drilling at least one fastener bore in the distal bone section and at least one fastener bore in the proximal bone section, each one of the fastener bores being located to be aligned with a corresponding one of the fastener holes located in the proximal and the distal bone sections when the fixation plate is positioned against the patient's bone.

In at least one embodiment, positioning the fixation plate against the patient's bone includes aligning the corresponding ones of the fastener holes with a corresponding one of the fastener bores.

According to yet another aspect, there is also provided a surgical kit for use in an osteotomy procedure, the surgical kit comprising: a surgical cutting guide superposable against a bone for guiding a cutting tool into the bone to cut the bone to thereby form a bone cut in the bone, the bone cut dividing the bone into first and second bone sections located on either side of the bone cut; a fixation plate for securing together the first and second bone sections in a predetermined angular orientation relative to each other, the fixation plate comprising: a first fixation portion having a bone interface side superposable against the first bone section and securable to the first bone section; a second fixation portion extending away from the first fixation portion, the second fixation portion having a bone interface side superposable against the second bone section and being securable to the second bone section, the second fixation portion including a holding portion, the bone interface side of the holding portion being shaped to conform to an outer surface of the second bone section when superposed thereto and when the first and second bone sections are configured in the predetermined angular orientation relative to each other such that a snug fit of the second bone section with the holding portion provides an indication that the first and second bone sections are in the predetermined angular orientation relative to each other.

In at least one embodiment, the surgical cutting guide is superposable against the bone for guiding the cutting tool into the bone to cut out a bone wedge portion from the bone to form a wedge opening in the bone and wherein the fixation plate is securable to the first and second bone sections following closing of the wedge opening with the first and second bone sections being adjacent to each other with a cutting plane interface extending thereinbetween.

In at least one embodiment, the surgical cutting guide includes first and second wedge cutting slots extending therethrough and defining a cutting path, the first and second wedge cutting slots being configured to receive and guide a cutting tool along the cutting path and into the bone.

In at least one embodiment, the surgical cutting guide includes at least one barrel, each barrel being configured and oriented to receive a mechanical fastener therein to secure the cutting guide to the bone prior to cutting out the wedge portion.

DETAILED DESCRIPTION

Figure 2:
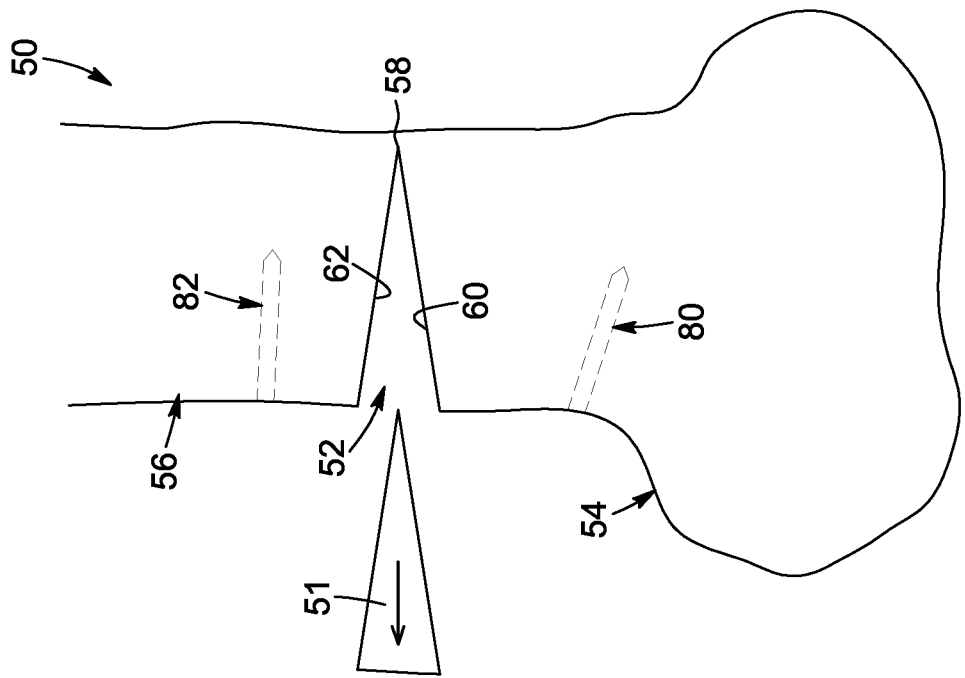
FIG. 2 is an elevation cross-sectional view of the patient's femur illustrated in FIG. 1, with the bone wedge portion removed to form a wedge opening defining distal and proximal bone sections.
Figure 1:
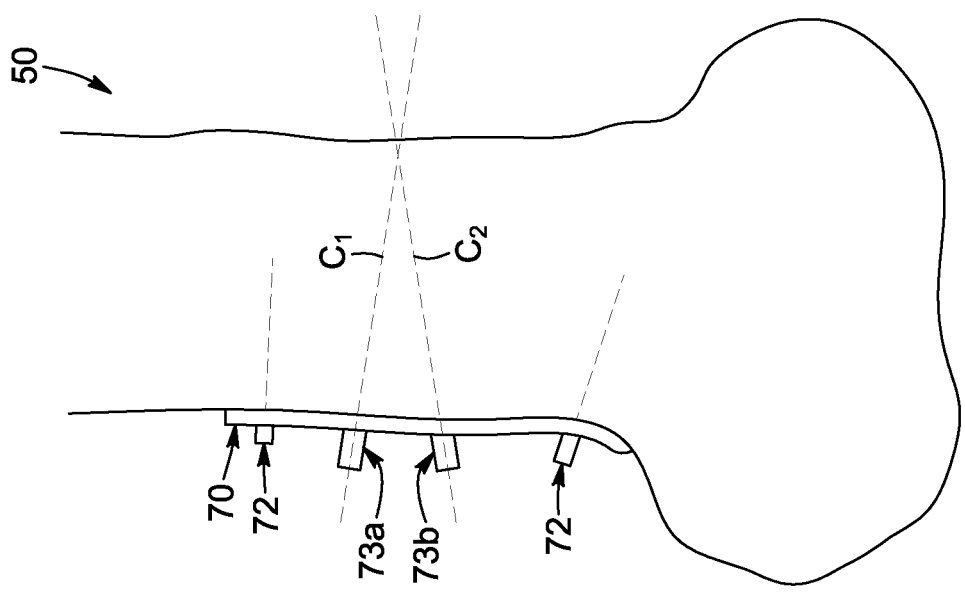
FIG. 1 is an elevation cross-sectional view of a patient's femur with a cutting guide placed against an outer surface of the femur and with cuts being made in the patient's femur to form a bone wedge portion in the femur, in accordance with one embodiment.

It will be appreciated that, for simplicity and clarity of illustration, where considered appropriate, reference numerals may be repeated among the figures to indicate corresponding or analogous elements or steps. In addition, numerous specific details are set forth in order to provide a thorough understanding of the exemplary embodiments described herein. However, it will be understood by those of ordinary skill in the art, that the embodiments described herein may be practiced without these specific details. In other instances, well-known methods, procedures and components have not been described in detail so as not to obscure the embodiments described herein. Furthermore, this description is not to be considered as limiting the scope of the embodiments described herein in any way but rather as merely describing the implementation of the various embodiments described herein.

For the sake of simplicity and clarity, namely so as to not unduly burden the figures with several references numbers, not all figures contain references to all the components and features, and references to some components and features may be found in only one figure, and components and features of the present disclosure which are illustrated in other figures can be easily inferred therefrom. The embodiments, geometrical configurations, materials mentioned and/or dimensions shown in the figures are optional, and are given for exemplification purposes only.

Referring to FIGS. 1 to 9, there is provided a fixation plate 100, shown in FIGS. 4 to 9, for use in an osteotomy procedure, in accordance with one embodiment. In FIGS. 1 to 9, the osteotomy procedure is a femoral osteotomy procedure. However, it is appreciated that the fixation plate can be designed and used for other osteotomy procedures, performed on other bones than a femur including and without being limitative, a tibia, a humerus, a radius/ulna (forearm) and multiple foot bones. It is appreciated that the shape and the configuration of the fixation plate will vary in accordance with the bone against which it is superposed.

Thus, in the paragraphs below, the fixation plate 100 and the osteotomy procedure are described in relation to a femoral osteotomy procedure as shown in FIGS. 1 to 9. However, it is appreciated that the osteotomy procedure can be performed on any suitable bone with a fixation plate configured to be superposed against an outer surface of the bone.

In the non-limitative embodiment shown in FIGS. 1 to 9, the fixation plate 100 is for use in a femoral closing-wedge osteotomy procedure performed on a patient's femur 50. This procedure includes cutting out a bone wedge portion 51 out of the femur 50 to form a wedge opening 52 in the femur 50, thereby dividing the femur 50 into distal and proximal bone sections 54, 56 located on either side of the wedge opening 52.

In the illustrated embodiment, the distal bone section 54 is located towards the femur's distal end and the proximal bone section 56 is located towards the femur's proximal end. It will be understood that the term "proximal end" used in relation to the femur 50 corresponds to the end of the femur 50 located towards the patient's hip joint and the term "distal end" used in relation to the femur 50 corresponds to the end of the femur 50 located away from the patient's hip joint.

More particularly, in the disclosure, the term "proximal" refers to a direction generally located toward the center of the body and nearest the point of attachment to the body. By opposition, the term "distal" refers to a direction away from the center of the body. In other words, in reference with a patient, the term "proximal" refers to a direction generally towards the torso of the patient and "distal" refers to a direction opposite of proximal, i.e. away from the torso of the patient. The term "anterior" refers to a direction generally toward the front of a patient and "posterior" refers to the opposite direction of anterior, i.e. toward the back of the patient. In the context of a fixation plate alone, such directions correspond to the orientation of the fixation plate after implantation. Thus, for instance, the proximal portion of the fixation plate is the portion which will be closest to the torso of the patient.

In the illustrated embodiment, the wedge opening 52 is formed by two substantially planar cuts $C_1$, $C_2$ made substantially along two cutting planes intersecting each other at an angle. The two substantially planar cuts thereby define a distal substantially planar bone section face 60 in the distal bone section 54 and a proximal substantially planar bone section face 62 in the proximal bone section 56 facing generally towards the distal substantially planar bone section face 60.

Still in the illustrated embodiment, the two substantially planar cuts $C_1$, $C_2$ forming the bone wedge portion 51 are located such that the distal bone section 54 includes the femur's distal epiphysis or distal femur and the proximal bone section 56 includes the femur's diaphysis or shaft adjacent the distal femur. Alternatively, the bone wedge portion 51 can instead be formed at another location along the femur 50 (or any suitable bone).

Still in the illustrated embodiment, the two substantially planar cuts $C_1$, $C_2$ are performed using a surgical cutting guide 70 placed against an outer surface of the femur 50. The cutting guide 70 is configured to guide one or more cutting tools into the femur 50 to perform the two substantially planar cuts $C_1$, $C_2$ at a desired position and at a desired angle relative to each other. In one embodiment, the cutting guide 70 can be patient-specific, i.e. be shaped to conform to exterior contours of the patient's femur 50 at a desired location. In this configuration, the cutting guide 70 may therefore be positionable solely at a unique predetermined location on the femur 50 where the cutting guide 70 conforms to the exterior contour of the femur, thereby reducing or eliminating the need to pre-measure and/or mark the femur to ensure that the cutting guide 70 is positioned at the desired location. Alternatively, the cutting guide 70 may not be patient-specific. In yet another embodiment, the two substantially planar cuts $C_1$, $C_2$ may not be performed using a cutting guide.

In the non-limitative embodiment shown wherein the two substantially planar cuts $C_1$, $C_2$ are performed using the cutting guide 70, the cutting guide 70 includes one or more barrels 72 configured and oriented to receive mechanical fasteners, such as screws, therein to secure the cutting guide 70 to the femur 50 prior to performing the cuts $C_1$, $C_2$. In the illustrated non-limitative embodiment, the cutting guide 70 includes two barrels 72 located on either side of the two substantially planar cuts $C_1$, $C_2$ to be performed. The mechanical fasteners can be inserted directly through the barrels 72 and into the femur 50 to secure the cutting guide 70 to the femur 50. In this embodiment, fastener bores 80, 82, shown in FIG. 2, are created by the insertion of the mechanical fasteners into the barrels 72 and the bone 50. Alternatively, the barrels 72 can be sized and shaped to receive and guide a drilling tool into the femur 50 at a predetermined angle and/or depth so as to pre-drill the fastener bores 80, 82 before the mechanical fasteners are inserted. The fastener bores 80, 82 may be used later in the surgical procedure, as will be explained further below. It will be understood that in other embodiments, the barrels 72 can include more or less than two barrels and that the barrels 72 can have a different configuration, shape and/or orientation.

As is known in the art, the cutting guide 70 also includes first and second wedge cutting slots 73a, 73b, extending therethrough and defining cutting paths. The wedge cutting slots 73a, 73b are configured to receive and guide a cutting tool along the cutting paths to perform the substantially planar cuts $C_1$, $C_2$ having the proper position, orientation, and/or depth into the femur 50.

In the embodiment shown, the wedge portion 51 does not extend through the entire cross-section of the femur 50. Instead, once the bone wedge portion 51 is removed from the femur 50, as shown in FIG. 2, the distal and proximal bone sections 54, 56 are still attached together by a substantially thin bone portion 58 located near the intersection of the two cutting planes $C_1$, $C_2$. The substantially thin bone portion 58 acts as a hinge about which the distal and proximal bone sections 54, 56 may pivot towards each other, as will be described in more details below.

Figure 3:
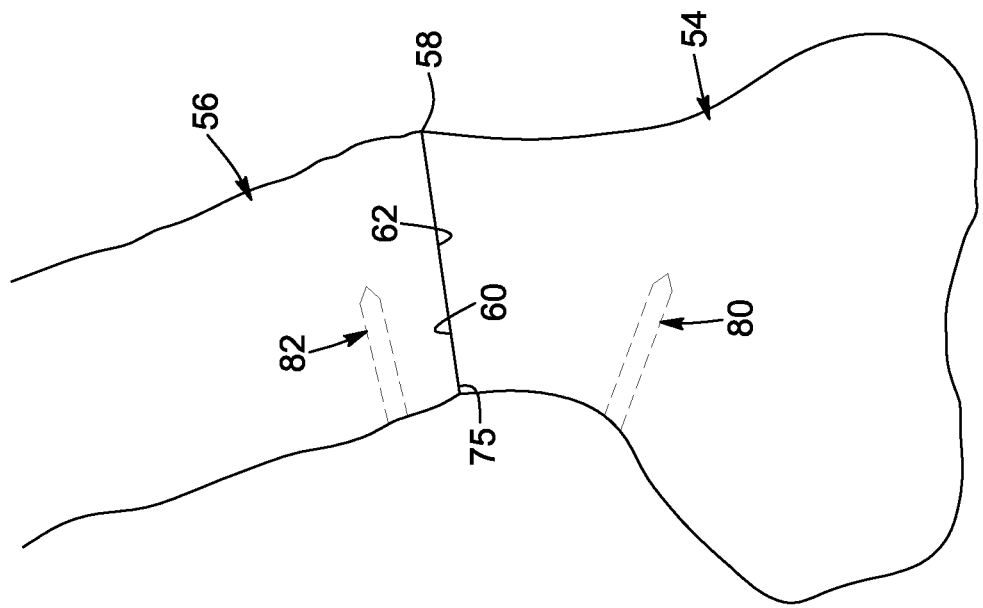
FIG. 3 is an elevation cross-sectional view of the patient's femur illustrated in FIG. 1, with the distal and proximal bone sections pivoted towards each other until they abut against each other.
Figure 4:
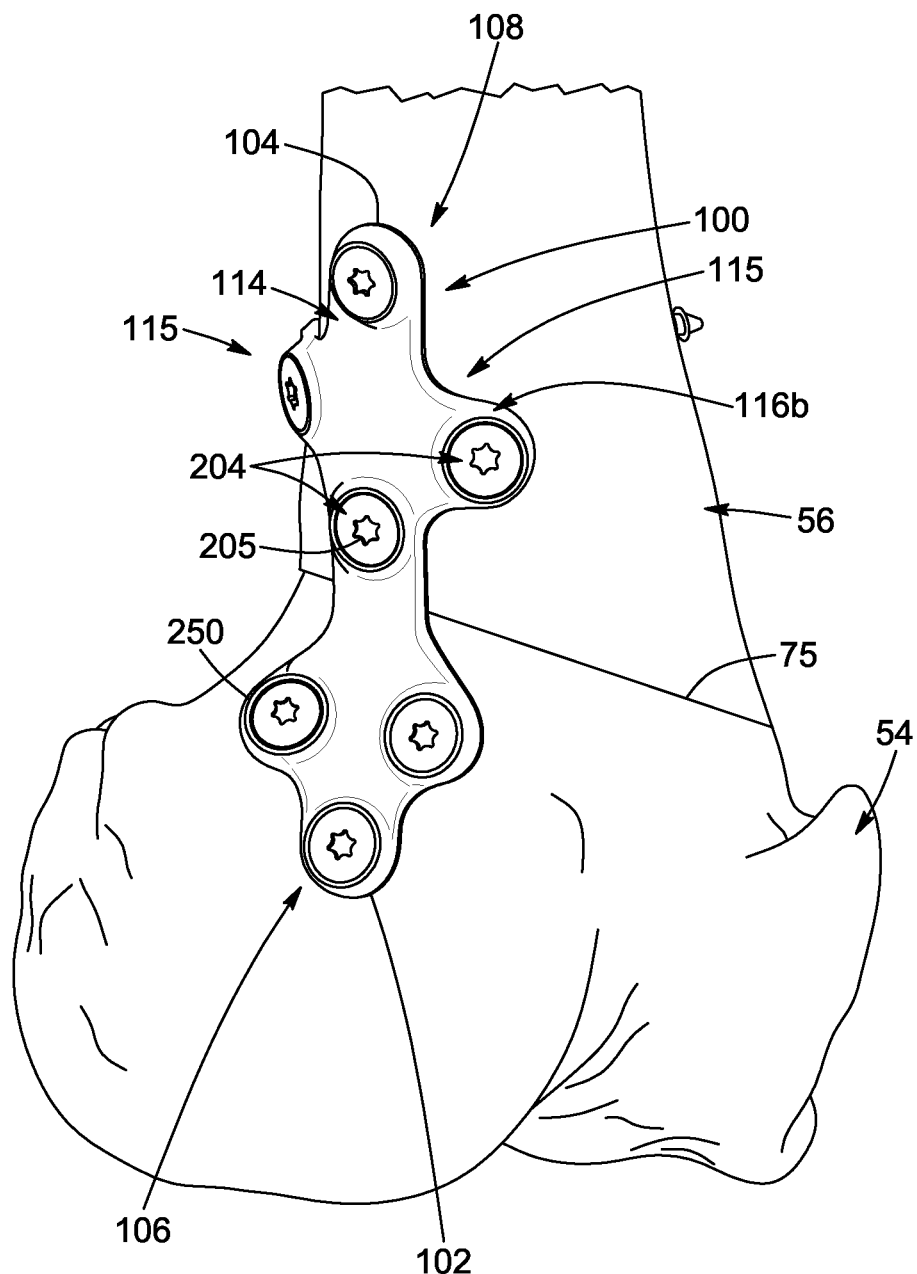
FIG. 4 is a perspective view of a fixation plate secured to the femur illustrated in FIG. 3, in accordance with one embodiment.
Figure 5:
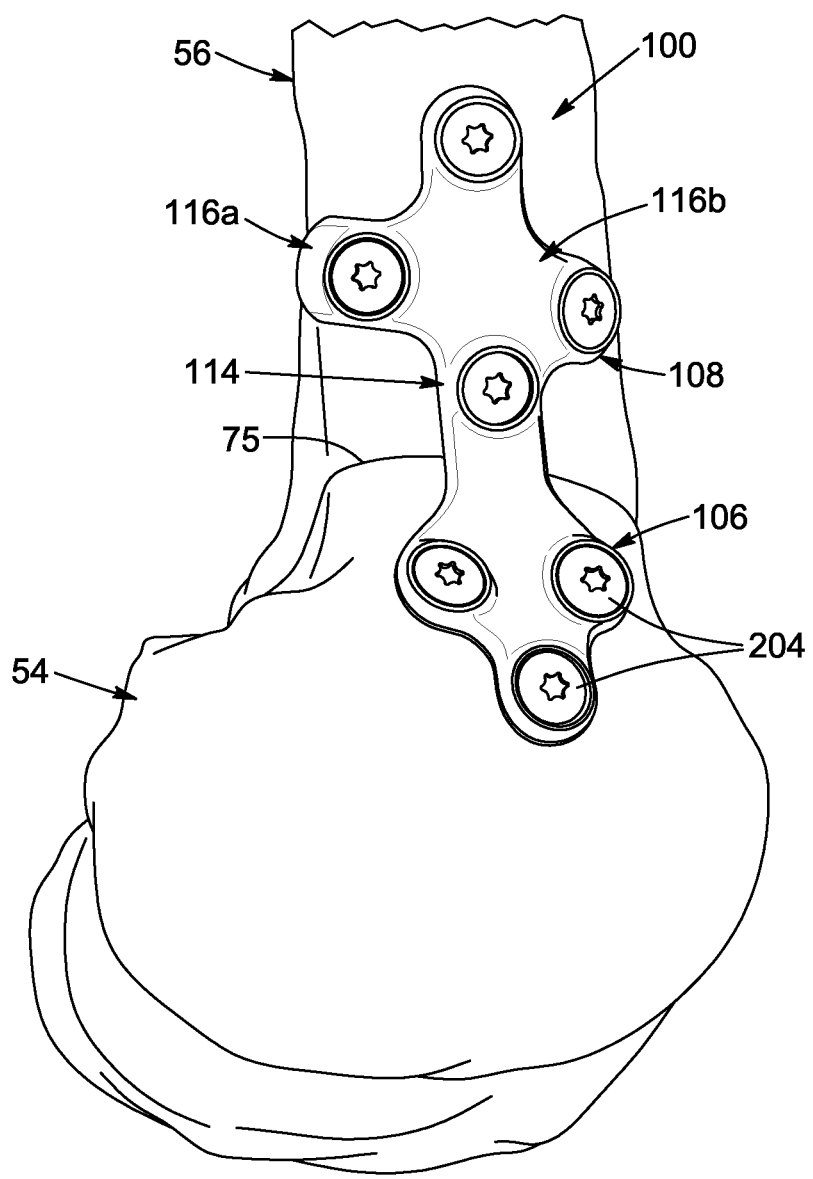
FIG. 5 is another perspective view of the fixation plate illustrated in FIG. 4, with the fixation plate secured to the femur.

The femoral osteotomy procedure is a closed-wedge osteotomy and further includes pivoting the distal and proximal bone sections 54, 56 towards each other until the distal and proximal bone sections 54, 56 abut each other, as shown in FIG. 3. In the illustrated embodiment, the distal and proximal bone sections 54, 56 are pivoted towards each other until the distal and proximal substantially planar bone section faces 60, 62 extend along each other (i.e. are superposed over each other with a cutting plane interface 75 defined thereinbetween), thereby closing the wedge opening 52.

Once the distal and proximal bone sections 54, 56 are pivoted such that they abut each other, the fixation plate 100 is secured to the distal and proximal bone sections 54, 56 to secure the distal and proximal bone sections 54, 56 together.

Referring more specifically to FIGS. 4 to 9, the fixation plate 100 is generally elongated in shape and includes a first or distal plate end 102 and a second or proximal plate end 104 located opposite the distal plate end 102. The fixation plate 100 further includes a first or distal fixation portion 106 located towards the distal plate end 102 and a second or proximal fixation portion 108 located towards the proximal plate end 104.

The fixation plate 100 is further configured such that when the fixation plate 100 is secured to the distal and proximal bone sections 54, 56, the distal fixation portion 106 overlaps (i.e. is superposed against) the distal bone section 54 and the proximal fixation portion 108 overlaps (i.e. is superposed against) the proximal bone section 56.

Figure 8:
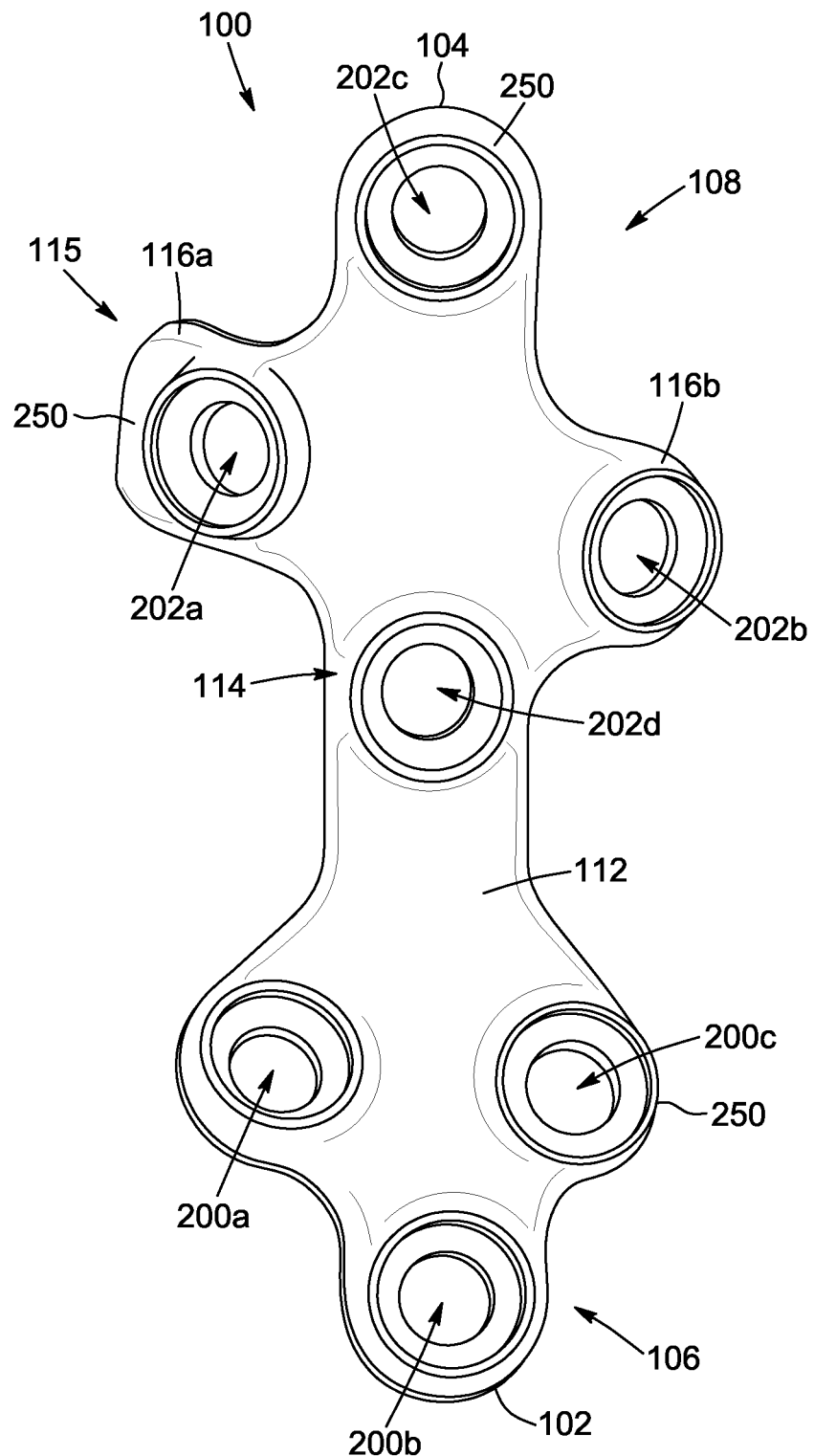
FIG. 8 is a front perspective view of the fixation plate illustrated in FIG. 4, shown in isolation.
Figure 9:
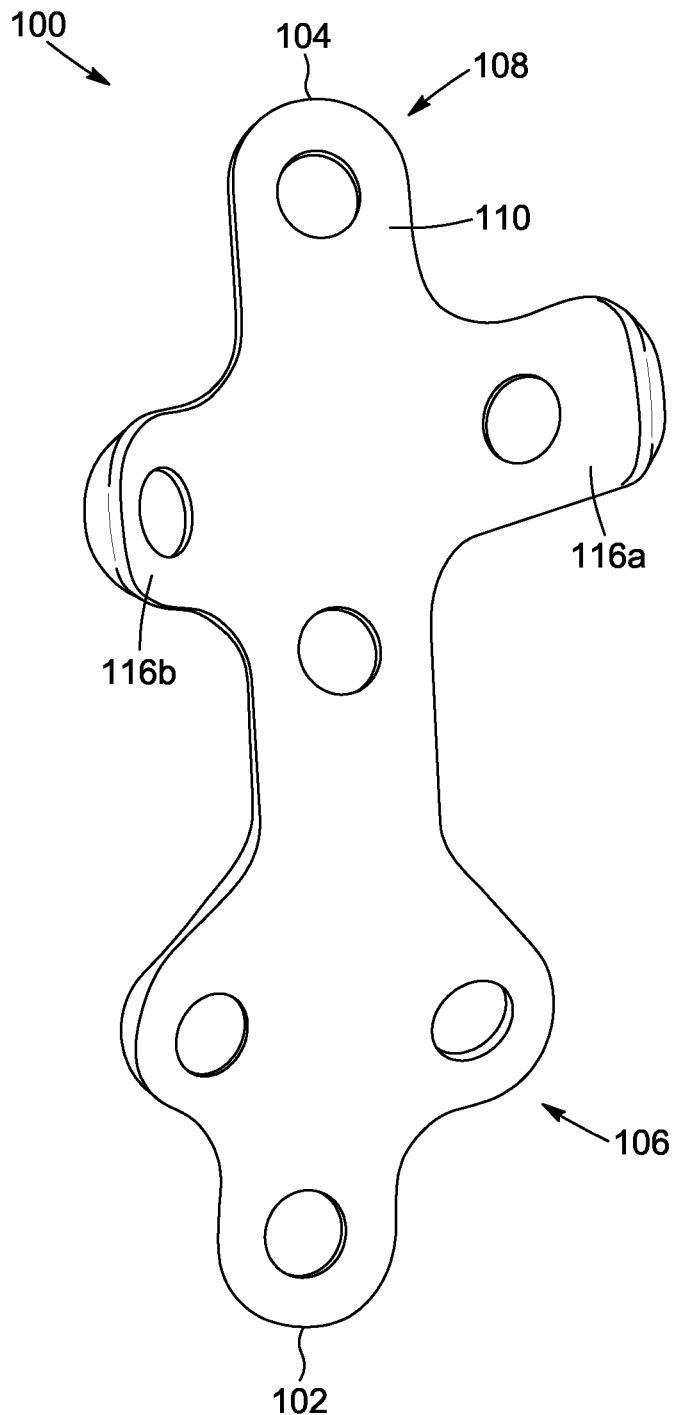
FIG. 9 is a rear perspective view of the fixation plate illustrated in FIG. 4, shown in isolation.

As shown in FIGS. 8 and 9, the fixation plate 100 includes a bone interface side 110 for positioning against an outer bone surface of the femur 50 and an outward facing side 112 opposite the bone interface side 110. In the illustrated embodiment, at least a portion of the bone interface side 110 is shaped to conform to a corresponding exterior contour of a predetermined location along a length of the femur such that the fixation plate 100 may only be positioned on the femur 50 at the predetermined location. In other words, the bone interface side 110 matches the outer surface of the femur 50 against which it is superposed. In this embodiment, the fixation plate 100 can therefore be patient-specific to provide a substantially snug fit with the patient's femur 50 once secured thereon. Specifically, prior to the femoral osteotomy procedure, the femur 50 can be scanned and a 3D model of the femur 50 or of a portion of the femur 50 can then be created in a virtual environment. The cutting and removal of the bone wedge portion 51 and the pivoting of the distal and proximal bone sections towards each other can then be planned and modeled on the 3D model of the femur 50. The location on the femur 50 where the fixation plate 100 is to be secured can then be determined, and the fixation plate 100 can then be designed in accordance with the exterior contour (or the shape of the outer surface) of the femur 50 at this determined location. The fixation plate 100 can then be manufactured using suitable manufacturing techniques such as CNC machining, additive manufacturing, bending and the like. This preoperative process allows the fixation plate 100 to be customized to the patient's femur 50 to ensure a snug fit therewith.

In the illustrated embodiment, the proximal fixation portion 108 is generally cross-shaped and includes an elongated central portion 114 and a holding portion 115 extending laterally away from the central portion 114 and along an outer surface of the femur 50. Specifically, the holding portion 115 includes first and second holding arms 116a, 116b extending laterally from either side of the central portion 114. Each holding arm 116a, 116b includes a free arm end 117 located away from the central portion 114 of the proximal fixation portion 108. When the fixation plate 100 is secured to the femur 50, the elongated central portion 114 extends substantially parallel to a bone axis extending longitudinally through a center of the femur 50 and the holding arms 116a, 116b extend in a substantially tangential direction along the outer surface of the proximal bone section 56 and around a portion of the proximal bone section 56. Specifically, the bone interface side 110 under the holding arms 116a, 116b is curved along a curvature corresponding to (or matching the curvature of) the outer surface of the proximal bone section 56. When the fixation plate 100 is secured to the femur 50, the holding arms 116a, 116b therefore extend away from either side of the central portion 114 and follow a curved outer surface of the proximal bone section 56 such that the holding arms 116a, 116b partially surround the proximal bone section 56.

In this configuration, the free arm ends 117 of the holding arms 116a, 116b are therefore spaced from each other.

Figure 6:
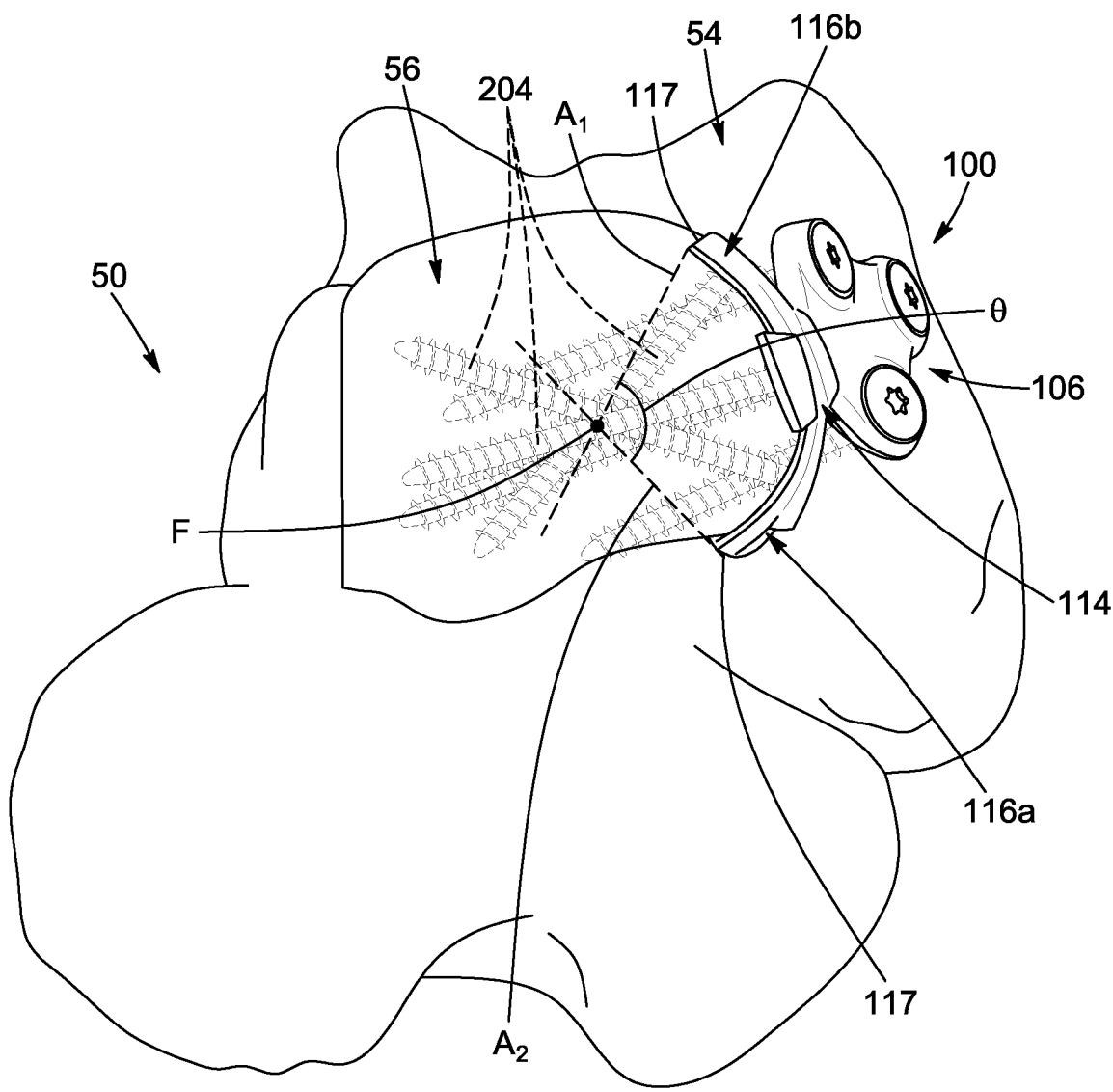
FIG. 6 is a top view of the fixation plate illustrated in FIG. 4, with the fasteners extending through the fixation plate and the femur being shown in broken lines.

Specifically, as shown in FIG. 6, the free arm ends 117 of the holding arms 116a, 116b are angled from each other at an arm spacing angle θ defined between a first arm axis A1 extending between the free arm end 117 of the first holding arm 116a and a substantial center F of the femur 50, and between a second arm axis A2 extending between the free arm end 117 of the second holding arm 116b and the substantial center F of the femur 50. It will be understood that instead of being defined between the free arm ends 117 and the substantial center F of the femur 50, the first and second arm axes A1, A2 can instead be defined between the free arm ends 117 and a localized center of curvature of the femur 50 of the predetermined location where the fixation plate 100 is to be secured.

It will be appreciated that the length of the arms, i.e. the distance between the free arm end 117 and the central portion 114, may be selected according to the shape and size of the patient's femur 50. Specifically, if the patient's femur 50 has a substantially large overall radius of curvature or localized radius of curvature at the predetermined location where the fixation plate 100 is to be secured, the length of the arms 116a, 116b, and therefore the arm spacing angle θ, may be substantially large (i.e. wide spacing angle θ), as well to ensure that the arms 116a, 116b surround partially the femur along a sufficiently large portion of the femur's outer surface. Alternatively, if the patient's femur 50 has a substantially small overall radius of curvature or localized radius of curvature at the predetermined location where the fixation plate 100 is to be secured, the length of the arms 116a, 116b, and therefore the arm spacing angle θ, may instead be substantially small (i.e. narrow spacing angle θ). For example, the arm spacing angle θ may be between about 15 degrees and 180 degrees. In a more specific embodiment, the arm spacing angle θ is smaller than about 110 degrees. In an embodiment, it may be between about 30 degrees and 110 degrees. In a still more specific embodiment, the arm spacing angle θ may be between about 40 degrees and 100 degrees.

It will also be appreciated that although the first and second holding arms 116a, 116b are substantially similar to each other in length and shape in the illustrated embodiment, the first and second holding arms 116a, 116b can instead be shaped and sized differently from each other.

To further assist in positioning the proximal fixation portion 108 relative to the proximal bone section 56, the bone interface side 110 under the elongated central portion 114 of the proximal fixation portion 108 can further also be shaped to conform to the outer surface of the proximal bone section 56. Alternatively, the bone interface side 110 under the elongated central portion 114 may not be shaped to conform to the outer surface of the proximal bone section 56.

It will be understood that in some instances, when the distal and proximal bone sections 54, 56 are pivoted towards each other, the substantially thin bone portion 58 acting as a hinge between the distal and proximal bone sections 54, 56 may twist or even break. In this event, the distal and proximal bone sections 54, 56 would therefore be able to rotate relative to each other about the bone axis, which can undesirably misalign the distal and proximal bone sections 54, 56 with each other.

To prevent misalignment of the distal and proximal bone sections 54, 56 with each other or to correct the alignment of the distal and proximal bone sections 54, 56 when the wedge opening 52 is closed, the predetermined curvature of the bone interface side 110 under the holding arms 116a, 116b can be selected such that the proximal bone section 56 can only snuggly fit against the proximal fixation portion 108 when the proximal bone section 56 is in a certain angular orientation relative to the proximal fixation portion 108, i.e. in a single and predetermined configuration/position which is determined during the preoperative planning. As mentioned above, the bone interface side 110 of the fixation plate 100 conforms to the shape of the outer surface of the femur 50 against which it is superposed. Thus, the bone interface side 110 of the holding arms 116a, 116b is also patient-specific and conforms to the shape of the outer surface of the femur 50 in a single and predetermined configuration, i.e. the configuration wherein the distal and proximal bone sections 54, 56 are aligned as planned during the preoperative planning.

This would allow the user performing the surgery to readily find the proper angular alignment of the distal and proximal bone sections 54, 56 with each other by confirming that the proximal bone section 56 is snuggly received in the holding arms 116a, 116b. In other words, a snug fit of the proximal bone section 56 in the holding arms 116a, 116b would provide an indication that the distal and proximal bone sections 54, 56 are at the predetermined angular orientation relative to each other.

If the distal and proximal bone sections 54, 56 are angularly misaligned with each other, the distal and proximal bone sections 54, 56 can be slightly rotated relative to each other until the proximal bone section 56 is snuggly received in the holding arms 116a, 116b.

Referring to FIGS. 8 and 9, there is shown that each fixation portion 106, 108 further includes at least one fastener hole 200, 202, each fastener hole 200, 202 being sized and shaped to receive a fastener 204, shown in FIGS. 4 to 7, for fastening the corresponding fixation portion 106 or 108 to a corresponding one of the distal and proximal bone sections 54, 56. Once the fixation plate 100 is positioned against the femur 50 and the distal and proximal fixation portions 106, 108 are respectively secured to the distal and proximal bone sections 54, 56 using the fasteners 204, the distal and proximal bone sections 54, 56 are therefore prevented from moving relative to each other.

In the non-limitative embodiment illustrated in FIGS. 1 to 9, the distal fixation portion 106 includes three distal portion fastener holes 200a, 200b, 200c disposed in a substantially triangular pattern. Alternatively, the distal fixation portion 106 can include more or less than three distal portion fastener holes 200a, 200b, 200c and the distal portion fastener holes 200a, 200b, 200c can be disposed according to any suitable pattern on the distal fixation portion 106.

Still in the non-limitative embodiment illustrated in FIGS. 1 to 9, the proximal fixation portion 108 includes four proximal portion fastening holes 202a, 202b, 202c, 202d disposed in a generally cross-shaped pattern on the proximal fixation portion 108. Specifically, the proximal fixation portion 108 includes first and second proximal portion fastening holes 202a, 202b located in each holding arm 116a, 116b, a third proximal portion fastening hole 202c located in the central portion 114 towards the proximal plate end 104 and a fourth proximal portion fastening hole 202d located in the central portion 114 generally centrally between the distal and proximal plate ends 102, 104. Alternatively, the proximal fixation portion 108 can include more or less than four proximal portion fastener holes 202a, 202b, 202c, 202d and the proximal portion fastener holes 202a, 202b, 202c, 202d can be disposed according to any suitable pattern on the proximal fixation portion 108.

In one embodiment, one or more fastener bores for receiving at least some of the fasteners 204 can further be predrilled into the femur 50 prior to positioning the fixation plate 100 against the femur 50. This configuration may assist the user in the positioning of the distal bone section 54

More specifically, the femoral osteotomy procedure can include drilling at least one distal fastener bore 80 through the distal bone section 54 and at least one proximal fastener bore 82 through the proximal bone section 56. In this embodiment, when the fixation plate 100 is positioned against the femur 50, at least one fastener hole 200 of the distal fixation portion 106 is alignable with a corresponding distal fastener bore 80 and at least one fastener hole 202 of the proximal fixation portion 108 is alignable with a corresponding proximal fastener bore 82. The fastener bores 80, 82 are further located such that when the corresponding fastener holes 200, 202 are aligned with the corresponding fastener bores 80, 82, the fixation plate 100 is in the predetermined location on the femur 50. The predrilled fastener bores 80, 82 thereby further assist the user in positioning the fixation plate 100 at the predetermined location on the femur 50 and in positioning the distal and proximal bone sections 54, 56 at the proper angular alignment with each other.

In the illustrated embodiment, the drilling of the fastener bores is performed prior to the pivoting of the distal and proximal bone sections 54, 56 towards each other using the cutting guide 70. Specifically, as mentioned above, the cutting guide 70 may include a plurality of barrels 72 configured and oriented to receive mechanical fasteners therein to secure the cutting guide 70 to the femur 50. Thus, in the non-limitative embodiment shown, the fastener bores 80, 82 correspond to the bores created in the femur 50 when securing the cutting guide 70 via the barrels 72 with mechanical fasteners, prior to performing the cuts $C_1$, $C_2$. In this embodiment, the fastener bores 80, 82 are therefore created by the insertion of mechanical fasteners into the barrels 72 and the femur 50, or by using a drilling tool received in the barrels 72 as described above. Alternatively, the drilling of the fastener bores may be performed without the assistance of the cutting guide 70, or with the assistance of a fastener bore drilling guide which is distinct from the cutting guide 70. In one embodiment, the procedure may not even include the drilling of fastener bores prior to positioning the fixation plate 100 against the femur 50.

In one embodiment, the at least one predrilled distal fastener bore includes a single distal fastener bore and the at least one proximal fastener bore includes a single proximal fastener bore. Alternatively, a plurality of distal fastener bores and/or a plurality of proximal fastener bores may be predrilled in the femur 50.

It will therefore be appreciated that the alignment of the fastener hole 200 of the distal fixation portion 106 with the corresponding distal fastener bore 80 ensures that the distal fixation portion 106 is positioned at the desired location on the distal bone section 54. In one embodiment, the bone interface side 110 under the distal fixation portion 106 may further be shaped to conform to an outer surface of the distal bone section 54 such that the distal fixation portion 106 may only be positioned on the femur 50 at the predetermined location. In another embodiment, the fastener hole 200 of the distal fixation portion 106 may not be alignable with a corresponding distal fastener bore 80 and the distal fixation portion 106 may only positionable in the desired location by matching the bone interface side 110 under the distal fixation portion 106 with the corresponding outer surface of the distal bone section 54 at the desired location. Alternatively, the bone interface side 110 at the distal fixation portion 106 may not be shaped to conform to the outer surface of the distal bone section 54.

In the illustrated embodiment, the fixation plate 100 further includes a plurality of grommet projections 250 extending away from the outward facing side 112 of the fixation plate 100, each grommet projection 250 surrounding a corresponding fastener hole 200, 202. The grommet projections 250 are sized and shaped to receive a fastener head 205 of the fastener 204 engaging the corresponding fastener hole 200, 202 such that the fastener head 205 is at least partially sunk in the grommet projection 250. In the illustrated embodiment, the fastener holes 200, 202 are substantially circular and the grommet projections 250 is also substantially circular. Alternatively, the fastener holes 200, 202 and the grommet projections 250 can be shaped according to any other suitable shape.

Each grommet projection 250 is further filleted to reduce or even eliminate any sharp edges from the outward facing side 112 of the fixation plate 100. To further reduce or even eliminate sharp edges from the fixation plate 100, an outer edge of the fixation plate 100 can further be chamfered. Alternatively, the fixation plate 100 may not include any grommet projection.

Figure 7:
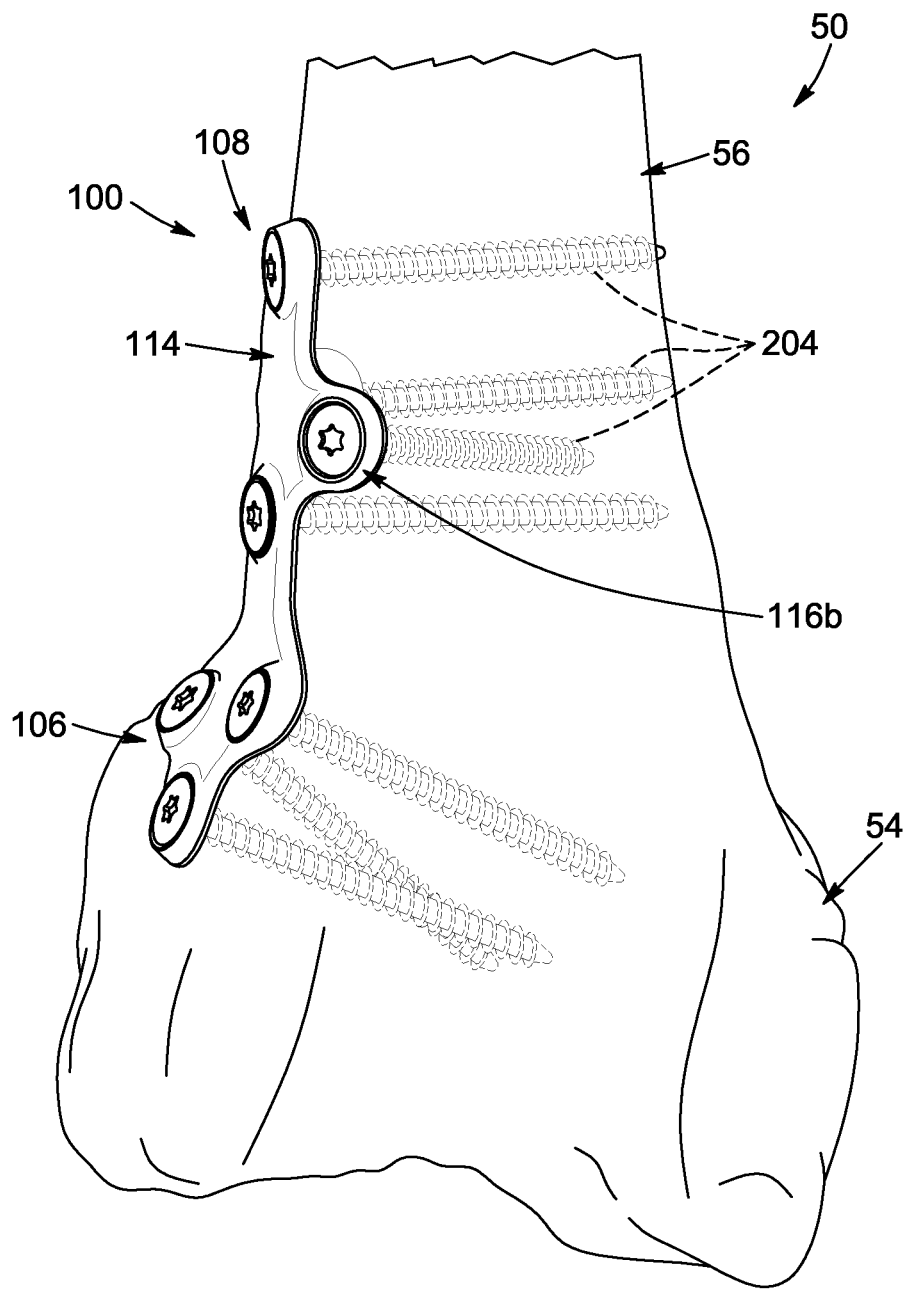
FIG. 7 is a side view of the fixation plate illustrated in FIG. 4, with the fasteners extending through the fixation plate and the femur being shown in broken lines.

In the illustrated embodiment, the holding arms 116a, 116b are generally aligned with each other on either side of the central portion 114 of the proximal fixation portion 108. In this configuration, the first and second proximal portion fastener holes 202, 202b are therefore disposed in a plane substantially perpendicular to the bone axis. As best shown in FIGS. 6 and 7, in this configuration, it may be necessary to angle the fasteners 204 extending through the first and second proximal portion fastener holes 202a, 202b slightly upwardly or downwardly towards the distal or proximal plate ends 102, 104 to prevent the fasteners 204 from interfering with each other when inserted in the proximal bone section 56.

It will be understood that the embodiment described above in connection with FIGS. 1 to 9 is only provided as an example, and that the fixation plate can have one of various alternative configurations.

Figure 10:
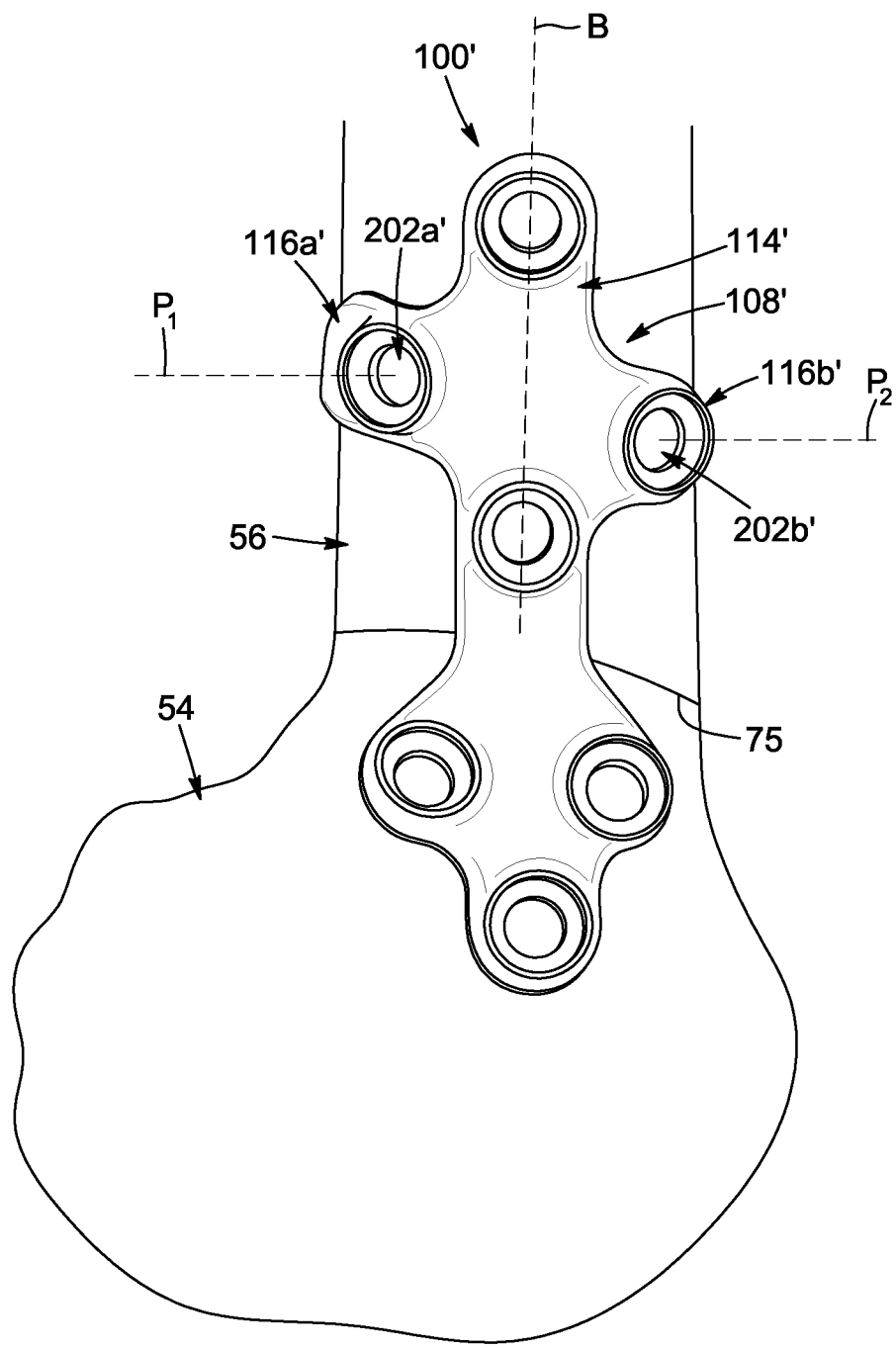
FIG. 10 is a schematic front elevation view of a fixation plate secured to a patient's femur, in accordance with another embodiment.

For example, FIG. 10 shows a fixation plate 100', in accordance with another embodiment. The fixation plate 100' is substantially similar to the fixation plate 100, except that the fixation plate 100' includes a proximal fixation portion 108' having a central portion 114' and first and second holding arms 116a', 116b' which are offset relative to each other along the central portion 114' rather than being aligned with each other on either side of the central portion 114'. In other words, the first holding arm 116a' includes a first proximal portion fastener hole 202a' which is generally positioned such that its center is disposed in a first hole plane $P_1$ extending perpendicular to the bone axis B and the second holding arm 116b' includes a second proximal portion fastener hole 202b' which is generally positioned such that its center is disposed in a second hole plane $P_2$ extending perpendicular to the bone axis B, the first and second hole planes $P_1$, $P_2$ being distinct from each other and spaced apart from each other along the bone axis B, i.e. they intersect the bone axis B at a different location. It will be appreciated that in this embodiment, fasteners 204 can be inserted substantially radially into the proximal bone section 56 through the first and second proximal portion fastener holes 202a', 202b' without interfering with each other, thereby eliminating the need to angle the fasteners 204 upwardly or downwardly as they enter the proximal bone section 56.

Figure 11:
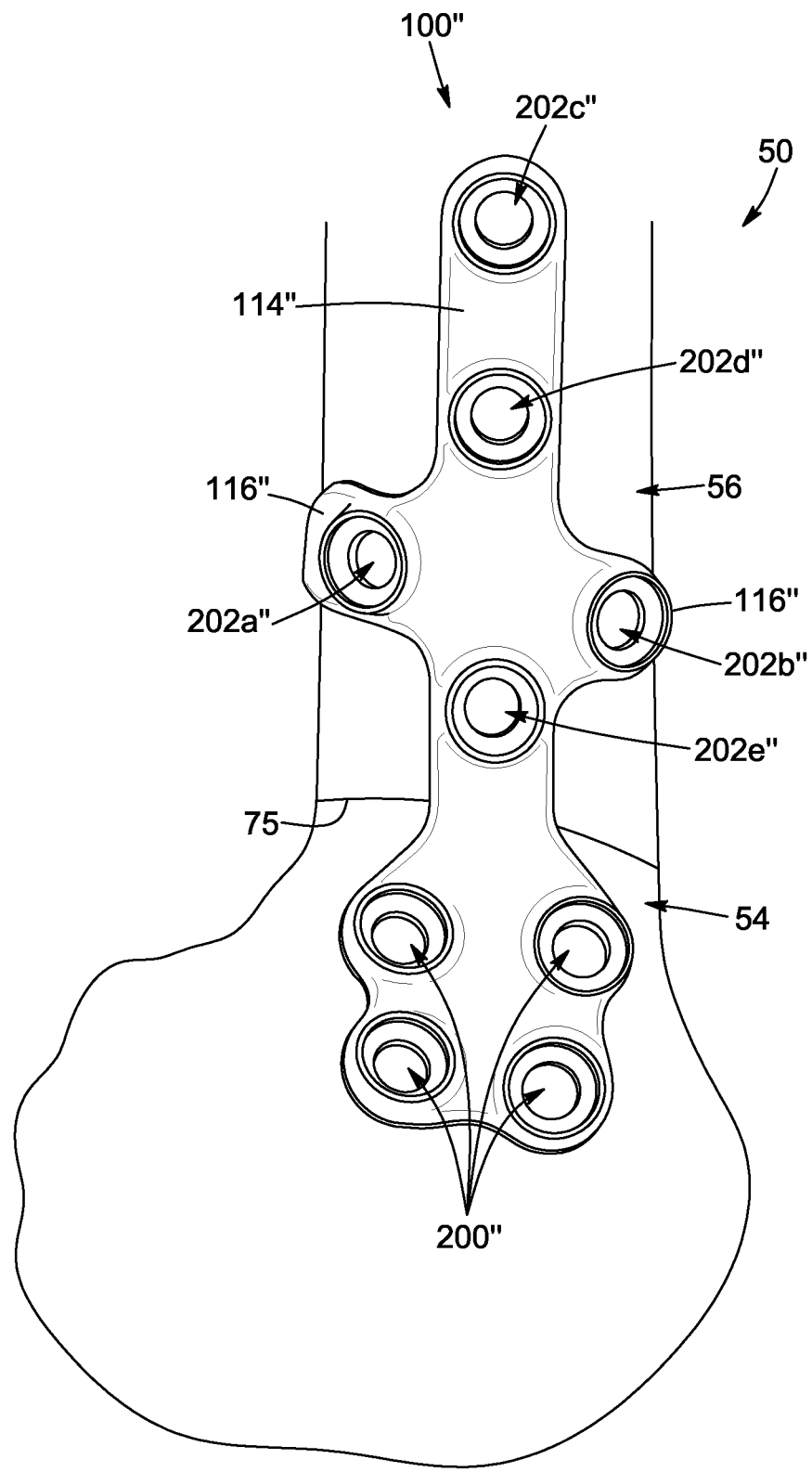
FIG. 11 is a schematic front elevation view of a fixation plate secured to a patient's femur, in accordance with yet another embodiment.

FIG. 11 shows a fixation plate 100", in accordance with yet another embodiment. The fixation plate 100" is generally similar to fixation plates 100 and 100' and includes a distal fixation portion 106" for securing to the distal bone section 54 and a proximal fixation portion 108" for securing to the proximal bone section 56. In this embodiment, the distal fixation portion 106" includes four fastener holes 200" instead of three. Alternatively, the distal fixation portion 106" can instead include any number of fastener holes that a skilled person would consider to be appropriate.

Still in the embodiment illustrated in FIG. 11, the proximal fixation portion 108" includes a central portion 114" and a pair of holding arms 116" which are offset relative to each other, similarly to the holding arms 116a', 116b' of the fixation plate 100'. Each holding arm 116" includes a fastener hole 202a", 202b". In this embodiment, the central portion 114" includes three fastener holes 202c", 202d", 202e" spaced from each other along the central portion 114". Alternatively, the central portion 114" can include more or less than three fastener holes.

In the three embodiments described above, the holding arms 116, 116', 116" are provided on the proximal fixation portion 108, 108', 108" of the fixation plates 100, 100', 100". However, it is appreciated that, in alternative embodiments (not shown), the holding arms 116, 116', 116" can be provided on the distal fixation portion 106, 106', 106". Still in another alternative embodiment, the holding arms 116, 116', 116" can be provided on the proximal fixation portion 108, 108', 108" and the distal fixation portion 106, 106', 106".

In the three embodiments described above, the fixation plates 100, 100', 100" include two holding arms 116, 116', 116", one on each side of the central portion 114, 114', 114". In an alternative embodiment (not shown), the fixation plate 100, 100', 100" can include only one holding arm 116, 116', 116" or more than two holding arms 116, 116', 116". In the embodiment shown, the holding arms 116, 116', 116" extend laterally from the proximal fixation portion 108, 108', 108" of the fixation plates 100, 100', 100". However, in an alternative embodiment, they can extend laterally from the distal fixation portion 106 of the fixation plates 100, 100', 100". Thus, in an embodiment, the distal fixation portion 106 of the fixation plates 100, 100', 100" can be cross-shaped. In an embodiment, only one of the proximal fixation portion 108, 108', 108" and the distal fixation portion 106 of the fixation plates 100, 100', 100" can include holding arms 116, 116', 116". In another embodiment, both the proximal fixation portion 108, 108', 108" and the distal fixation portion 106 of the fixation plates 100, 100', 100" can include holding arms 116, 116', 116".

In the embodiment shown, the fixation plates 100, 100', 100" are used for a closed wedge osteotomy. However, it is appreciated that the fixation plates 100, 100', 100" including holding arms 116, 116', 116" extending laterally from the central portion 114, 114', 114" in the proximal fixation portion 108, 108', 108" and/or the distal fixation portion 106 can be used an open wedge osteotomy.

For an open wedge osteotomy, the distal and proximal bone sections 54, 56 are not pivoted towards each other but remain spaced-apart with an opening, typically wider than the wedge opening 52, located thereinbetween. Thus, the distal and proximal bone sections 54, 56 are separated by a bone cut when the fixation plate is secured to the bone.

In one embodiment, any one of the fixation plates 100, 100', 100" described above and configured according to any of the embodiments described above can be provided together with the surgical cutting guide 70 configured as described above as a surgical kit for use in an osteotomy procedure, such as and without being limitative a femoral osteotomy procedure. The kit can further include one or more cutting tools to perform the two substantially planar cuts in the bone to form the wedge and/or one or more drilling tools to predrill the fastener bores 80, 82. The kit can further include any other component that a skilled person would consider to be suitable for an osteotomy procedure.

While the above description provides examples of the embodiments, it will be appreciated that some features and/or functions of the described embodiments are susceptible to modification without departing from the spirit and principles of operation of the described embodiments. Accordingly, what has been described above has been intended to be illustrative and non-limiting and it will be understood by persons skilled in the art that other variants and modifications may be made without departing from the scope of the invention as defined in the claims appended hereto.

What is claimed is:

1. A fixation plate for securing together adjacent first and second bone sections of a bone having a bone cut extending thereinbetween to realign the first bone section with respect to the second bone section according to a predetermined angular orientation, the bone extending along a bone axis, the fixation plate comprising:
   a first fixation portion having a bone interface side superposable against the first bone section and securable to the first bone section, the bone interface side of the first fixation portion being shaped to conform to a corresponding outer surface of the first bone section when superposed thereto;
   a second fixation portion extending away from the first fixation portion, the second fixation portion having a bone interface side superposable against the second bone section and being securable to the second bone section, the second fixation portion including:
      an elongated central portion extending substantially parallel to the bone axis when the fixation plate is secured to the first and second bone sections; and
      first and second holding arms extending laterally from either side of the elongated central portion, the bone interface side of each holding arm being shaped to conform to a corresponding outer surface of the second bone section when superposed thereto,
      wherein each one of the holding arms is curved to partially surround the second bone section and the bone interface sides of the central elongated portion and each one of the holding arms of the second fixation portion, and the bone interface side of the first fixation portion, are shaped to simultaneously snuggly fit against the second bone section, and the first bone section, respectively, only when the first and second bone sections are oriented at the predetermined angular orientation relative to each other with the bone cut extending between the first and the second bone sections, wherein each one of the first and second holding arms includes a free arm end located away from the elongated central portion and wherein the first and second holding arms are sized and shaped such that when the first fixation portion is superposed against the first bone portion and the second bone portion is superposed against the second fixation portion, the first holding arm defines a first arm axis extending between the free arm end of the first holding arm and a substantial center of the bone and the second holding arm defines a second arm axis extending between the free arm end of the second holding arm and the substantial center of the bone, the first and second arm axes are angled away from each other at an arm spacing angle ranging between about 15 degrees and about 180 degrees, wherein the elongated central portion includes a pair of lateral edges and each holding arm includes a fastener hole that is spaced laterally outward of an adjacent one of the lateral edges, wherein each fastener hole is sized and shaped for a respective fastener to secure the fixation plate to the bone.

2. The fixation plate as claimed in claim 1, wherein the first and second holding arms are in alignment with each other along the elongated central portion.

3. The fixation plate as claimed in claim 1, wherein the first and second holding arms are offset from each other along the elongated central portion.

4. The fixation plate as claimed in claim 1, wherein the second fixation portion is substantially cross-shaped.

5. The fixation plate as claimed in claim 1, wherein the arm spacing angle is between about 20 degrees and about 150 degrees.

6. The fixation plate as claimed in claim 5, wherein the arm spacing angle is between about 30 degrees and about 110 degrees.

7. The fixation plate as claimed in claim 6, wherein the arm spacing angle is between about 40 degrees and about 100 degrees.

8. The fixation plate as claimed in claim 1, wherein the arm spacing angle is less than about 110 degrees.

9. The fixation plate as claimed in claim 1, wherein the first fixation portion is a distal fixation portion and the second fixation portion is a proximal fixation portion.

10. The fixation plate as claimed in claim 9, wherein the fixation plate includes a plurality of fastener holes sized and shaped for receiving fasteners to secure the fixation plate to the bone, the plurality of fastener holes including at least one distal portion fastener hole defined in the distal fixation portion and at least one proximal portion fastener hole defined in the proximal fixation portion.

11. The fixation plate as claimed in claim 10, wherein the at least one distal portion fastener hole includes at least three distal portion fastener holes.

12. The fixation plate as claimed in claim 10, wherein the plurality of fastener holes included in the fixation plate comprises at least one central portion fastener hole defined in the elongated central portion of the proximal fixation portion.

13. The fixation plate as claimed in claim 10, further comprising an outward facing side located opposite the bone interface side of the first and second fixation portions, the fixation plate further comprising a plurality of grommet projections extending away from of the outward facing side, each grommet projection surrounding a corresponding one of the fastener holes.

14. The fixation plate as claimed in claim 1, wherein the first and second holding arms extend in a plane which extends substantially perpendicular to the bone axis.

15. A surgical kit for use in an osteotomy procedure, the surgical kit comprising:
a surgical cutting guide superposable against a bone for guiding a cutting tool into the bone to cut the bone to thereby form a bone cut in the bone, the bone cut dividing the bone into first and second bone sections located on either side of the bone cut; and
the fixation plate of claim 1.

16. The surgical kit as claimed in claim 15, wherein the surgical cutting guide is superposable against the bone for guiding the cutting tool into the bone to cut out a bone wedge portion from the bone to form a wedge opening in the bone and wherein the fixation plate is securable to the first and second bone sections following closing of the wedge opening with the first and second bone sections being adjacent to each other with a cutting plane interface extending therebetween.

17. The surgical kit as claimed in claim 16, wherein the surgical cutting guide includes first and second wedge cutting slots extending therethrough and defining a cutting path, the first and second wedge cutting slots being configured to receive and guide a cutting tool along the cutting path and into the bone.

18. The surgical kit as claimed in claim 15, wherein the surgical cutting guide includes at least one barrel, each barrel being configured and oriented to receive a mechanical fastener therein to secure the cutting guide to the bone prior to cutting out the wedge portion.

19. An osteotomy fixation plate for securing together adjacent first and second bone sections of a bone having a bone cut extending therebetween to realign the first bone section with respect to the second bone section according to a predetermined angular orientation, the bone extending along a bone axis, the osteotomy fixation plate comprising:
a first fixation portion securable to the first bone section;
a second fixation portion extending away from the first fixation portion and being securable to the second bone section, the second fixation portion including:
an elongated central portion extending substantially parallel to the bone axis when the fixation plate is secured to the first and second bone sections; and
first and second holding arms extending laterally from either side of the elongated central portion and being curved to partially surround the second bone section, each one of the first and second holding arms includes a free arm end located away from the elongated central portion,
wherein the osteotomy fixation plate has a bone interface side superposable to the bone and extending along the first fixation portion and the first and second holding arms and the elongated central portion of the second fixation portion, the bone interface side being shaped to simultaneously snuggly fit against the first bone section, and the second bone section, respectively, only when the first and second bone sections are oriented at the predetermined angular orientation relative to each other with the bone cut extending between the first and the second bone sections, wherein the first and second holding arms are sized and shaped such that when the first fixation portion is superposed against the first bone portion and the second bone portion is superposed against the second fixation portion, the first holding arm defines a first arm axis extending between the free arm end of the first holding arm and a substantial center of the bone and the second holding arm defines a second arm axis extending between the free arm end of the second holding arm and the substantial center of the bone, the first and second arm axes are angled away from each other at an arm spacing angle ranging between about 15 degrees and about 180 degrees.

* * * * *